(12) United States Patent
Razavi

(10) Patent No.: US 7,250,478 B2
(45) Date of Patent: Jul. 31, 2007

(54) SILICON CONTAINING CYCLOPENTADIENYL RING FOR METALLOCENE CATALYST COMPONENTS

(75) Inventor: Abbas Razavi, Mons (BE)

(73) Assignee: TOTAL Petrochemicals Research Feluy, Feluy (BE)

( * ) Notice: Subject to any disclaimer, the term of this patent is extended or adjusted under 35 U.S.C. 154(b) by 151 days.

(21) Appl. No.: 10/529,248

(22) PCT Filed: Sep. 24, 2003

(86) PCT No.: PCT/EP03/10713

§ 371 (c)(1),
(2), (4) Date: Aug. 22, 2005

(87) PCT Pub. No.: WO2004/029107

PCT Pub. Date: Apr. 8, 2004

(65) Prior Publication Data

US 2006/0014634 A1    Jan. 19, 2006

(30) Foreign Application Priority Data

Sep. 27, 2002   (EP)   .................................. 02079065

(51) Int. Cl.
C08F 4/58 (2006.01)
C07F 17/02 (2006.01)
B01J 31/38 (2006.01)

(52) U.S. Cl. ...................... 526/126; 526/160; 526/170; 526/351; 526/352; 526/943; 556/11; 556/12; 556/43; 556/53; 556/58; 502/103; 502/117

(58) Field of Classification Search ................... 556/53, 556/58, 43, 12, 11; 502/103, 117; 526/160, 526/170, 126, 352, 351

See application file for complete search history.

(56) References Cited

U.S. PATENT DOCUMENTS 4,892,851 A   1/1990 Ewen et al.
5,719,241 A   2/1998 Razavi et al.

(Continued)

FOREIGN PATENT DOCUMENTS

EP   0 277 004 A1   8/1988
EP   0 426 643 A1   5/1991

(Continued)

OTHER PUBLICATIONS

JP 8-245715 (abstract and translation in English).*
Dysard et al., J. Am. Chem. Soc. 200, 122, 3097-3105.*

(Continued)

Primary Examiner—David W. Wu
Assistant Examiner—Rip A. Lee
(74) Attorney, Agent, or Firm—William D. Jackson

(57) ABSTRACT

The present invention refers to a metallocene catalyst component for producing polyolefins according to formula (I) $R''_s (CpR_n)_g (CpR_n) M Q_{3-g}$ (I) or according to formula (II) $R''(CpR_n)MeXQ$ (II) wherein—each Cp is a substituted or unsubstituted cyclopentadienyl ring with the bridge-head position of at least one of the cyclopentadienyl rings being occupied by a silicon atom;—each R is the same or different and is hydrogen or a hydrocarbyl radical such as alkyl, alkenyl, aryl, alkylaryl or arylalkyl radical containing from 1 to 20 carbon atoms or two carbon atoms are joined together to form a C4-C6 ring; —R" is a structural bridge between two Cp rings;—M is a group IIIB, IVB, VB or VIB metal;—Q is a hydrocarbyl radical such as aryl, alkyl, alkenyl, alkylaryl or arylalkyl radical having from 1 to 20 carbon atoms, a hydrocarboxy radical having from 1 to 20 carbon atoms or a halogen and can be the same or different from each other;—s is 0 or 1, g is 0, 1 or 2 and s is 0 when g is 0, n is 4 when s is 1 and n is 5 when s is 0, —X is an hetero atom ligand with one or two lone pair electrons and selected from the group VA or VIA, substituted or unsubstituted. Said metallocene catalyst component is used in a catalyst system for preparing polyolefins with desired properties.

26 Claims, 3 Drawing Sheets

U.S. PATENT DOCUMENTS

| | | | |
|---|---|---|---|
| 6,114,481 | A | 9/2000 | McMeeking et al. |
| 6,448,349 | B1 | 9/2002 | Razavi |
| 6,608,224 | B2 * | 8/2003 | Resconi et al. ............... 556/27 |
| 6,630,550 | B1 | 10/2003 | Razavi |
| 6,855,782 | B2 | 2/2005 | Shamshoum et al. |

FOREIGN PATENT DOCUMENTS

| | | |
|---|---|---|
| EP | 0 427 696 A2 | 5/1991 |
| JP | 8-245715 * | 9/1996 |
| WO | WO 91/03500 A1 | 3/1991 |
| WO | WO 98/02469 A1 | 1/1998 |

OTHER PUBLICATIONS

Dysard et al., Synthesis and Reactivity of n5-Silolyl, n5-Germolyl, and n5-Germole Dianion Complexes of Zirconium and Hafnium, Journal of the American (cont'd) Chemical Society, 2000, pp. 3097-3105, vol. 122, American Chemical Society, published on internet Mar. 18, 2000.

Watanabi et al., Reaction of Trimethylaluminum with [(tBu)Al(u3-O)]6: Hybrid tert-Butylmethylalumoxanes as Cocatalysts for Olefin Polymerization, (cont'd) Organometallics, 2001, pp. 460-467, vol. 20, American Chemical Society, published on internet Jan. 5, 2001.

Dysard et al., n5-Silolyl and n5-Germolyl Complexes of d0 Hafnium, Structural Characterization of an n5-Silolyl Complex, Journal of the American Chemical (cont'd) Society, 1998, pp. 8545-8246, vol. 120, American Chemical Society, published on internet Jul. 31, 1998.

Liu et al., Structure and Chemistry of 1-Silafluorenyl Dianion, Its Derivatives, and an Organosilicon Diradical Dianion, Journal of the American Chemical Society, (cont'd) 2002, pp. 49-57, vol. 124, No. 1, American Chemical Society, published on internet Dec. 6, 2001.

Francis, et al., "Hydroalumination of H2C=CHCH2SMe: Synthesis and Molecular Structure of (tBu)2Al(CH2CH2CH2Sme)," Main Group (cont'd) Chemistry, 1999, vol. 3, pp. 53-57, Overseas Publishers Association, Malaysia.

Francis, et al., "Are intramolecularly stabilized compounds of aluminum suitable structural models of the SN2 transition state? Molecular structure (cont'd) of [(tBu)2Al(u-OC6H4-2-OMe)]2," Polyhedron, vol. 18, pp. 2211-2218, Elsevier Science Ltd.

* cited by examiner

SILICON CONTAINING CYCLOPENTADIENYL RING FOR METALLOCENE CATALYST COMPONENTS

The present invention relates to a catalyst component and a catalyst system for use in the preparation of polyolefins, especially isotactic or syndiotactic polyolefins. The invention further relates to a process for the polymerisation of olefins using the catalyst component in a catalyst system.

In order to improve the properties of resins, bridged metallocene catalyst systems were developed. They are disclosed for example in PCT application WO91/03500. Typical bridged metallocene components are ethylene bis indenyl zirconium dichloride or ethylene bis tetrahydroindenyl zirconium dichloride, or they comprise substituted cyclopentadienyl such as disclosed in U.S. Pat. No. 4,892,851. In these metallocene components, the bridge and the substitutents' size and position were selected with a view to controlling the stereochemistry of polypropylene.

Resins produced with these improved metallocene catalysts components display improved mechanical properties because of their high molecular weight. In addition they have improved processing capabilities because of the presence of long chain branches. There is however room for improvement.

In addition, these catalyst components are generally unstable at high temperature thereby placing an upper limit on the temperature that can be employed in a polymerisation reaction. The catalyst component decomposes if the polymerisation temperature is too high.

Recent work has studied the behaviour of catalyst systems comprising carbon-containing ligands having heteroatoms in their structure. U.S. Pat. No. 6,114,481 for example discloses compounds in which an organometallic complex is formed from a group IV metal and a ketimide ligand. These types of compounds have been found useful in the preparation of olefin co-polymers having high molecular weight and very low density. Ketimide metal complexes have the general formula

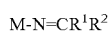

wherein M is the metal atom and R1 and R2 are substituents.

U.S. Pat. No. 6,051,667 discloses metallocene catalyst component comprising a phospholyl ligand. The metallocene components comprise two cyclopentadiene-type ligands, one of which being a phospholyl ligand, joined to each other by a metalloid-containing group. The bridging group is attached to the phospholyl ligand at the carbon atom adjacent to the phosphorous atom. These catalyst components are useful in the polymerisation of polymer comprising ethylene and propylene and more particularly linear low density polyethylene (LLDPE).

These catalyst systems can further be improved and more particularly, there is a need to prepare catalyst systems capable of producing macro chains having new polymeric properties.

This invention discloses the use of silicon containing cyclopentadienyl rings to prepare bridged or unbridged structures comprising cyclopentadienyl, fluorenyl, or indenyl components, substituted or unsubstituted, for the preparation of metallocene catalyst components.

The metallocene components of the present invention have a structure according to the formula:

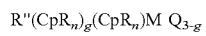

wherein
  each Cp is a substituted or unsubstituted cyclopentadienyl ring with the bridge-head position of at least one of the cyclopentadienyl rings being occupied by a silicon atom;
  each R is the same or different and is hydrogen or a hydrocarbyl radical such as alkyl, alkenyl, aryl, alkylaryl or arylalkyl radical containing from 1 to 20 carbon atoms or two carbon atoms are joined together to form a C4-C6 ring;
  R" is a structural bridge between two Cp rings;
  M is a group IIIB, IVB, VB or VIB metal;
  Q is a hydrocarbyl radical such as aryl, alkyl, alkenyl, alkylaryl or arylalkyl radical having from 1 to 20 carbon atoms, a hydrocarboxy radical having from 1 to 20 carbon atoms or a halogen and can be the same or different from each other;
  g is 1 or 2 and n is an integer from 0 to 4.

In the prior art, the silicon atom was placed in the bridge of the metallocene catalyst component whereas in the present invention, it is placed in the cyclopentadienyl ring and replaces the carbon atom located at the bridge-head position in the cyclopentadienyl ring. The silicon atom is larger and has a larger number of electrons than the carbon atom. There are therefore more possibilities to vary the angle of aperture and the electronic character of the metallocene catalyst component with a silicon atom present in the cyclopentadienyl ring than with a carbon atom.

By substituted, it is meant that any of the positions on the cyclopentadienyl derivative may comprise a substituent in place of a hydrogen atom. This may be either within the five-membered cyclopentadienyl ring or, if the ligand is for example an indenyl, a tetrahydroindenyl or a fluorenyl, this may be on a carbon atom in the ring system outside of the five-membered ring.

Each catalyst component comprises two or more cyclopentadienyl derivatives that may be the same or different.

The particular cyclopentadienyl ligands on the metallocene catalyst lead to the advantage of the present invention.

In the present invention, the type of cyclopentadienyl derivative is not especially limited, provided that the derivative comprises at least one five-membered cyclopentadienyl-type ring wherein the bridgehead position is occupied by a silicon atom. Thus, in preferred embodiments of the present invention, the Cp's may be independently selected from cyclopentadienyl-type groups, indenyl-type groups and fluorenyl-type groups. In the present disclosure, cyclopentadienyl-type group is meant to be a single substituted or unsubstituted cyclopentadienyl ring system and not a fused ring system such as indenyl or fluorenyl systems.

The type of bridge present between the ligands in the present catalyst component is not particularly limited. Typically R" comprises an alkylidene group having from 1 to 20 carbon atoms, a germanium group (e.g. a dialkyl germanium group), a silicon group (e.g. a dialkyl silicon group), a siloxane group (e.g. a dialkyl siloxane group), an alkyl phosphine group or an amine group. Preferably, the substituent on the bridge comprises a hydrocarbyl radical having at least one carbon, such as a substituted or unsubstituted ethylenyl radical, for example —$CH_2$—$CH_2$— (Et). Most preferably R" is Et or $Me_2Si$.

The metal M in the metallocene component is preferably a metal from group IIIB, IVB, VB or VIB of the periodic table. Typically, M is Ti, Zr, Hf or V. Preferably, it is Ti or Zr and most preferably, it is Zr.

Q is preferably a halogen and most preferably it is Cl.

The substituent or substituents present on the ligands are not particularly limited. If there is more than one substiutent, they can be the same or different. Typically, they are independently selected from an hydrocarbyl group having from 1 to 20 carbon atoms. Amongst the preferred substituents, one can cite methyl (Me) groups, phenyl (Ph), benzyl (Bz), naphtyl (Naph), indenyl (Ind), benzendyl (BzInd), as well as Et, n-propyl (n-Pr), iso-propyl (I-Pr), n-butyl (n-Bu-, tert-butyl (t-Bu), silane derivatives (e.g. $Me_3Si$), alkoxy preferably given by the formula R—O where R is an alkyl having from 1 to 20 carbon atoms, cycloalkyl and halogen. Preferably there are at most two substituents on each Cp ring.

The position of the substituent or substituents on the ligands is not particularly limited. The ligands may thus have any substitution pattern including unsubstituted or fully substituted. However, when Cp is a cyclopentadienyl-type group, the substituents are preferably in the 3- and/or 5-positions or in the 2- and/or 4-positions. When Cp is a fluorenyl-type group, the substituents are preferably in the 3- and/or 6-positions or in the 2- and/or 7-positions. When Cp is an indenyl-type group, the substituents are preferably in the 2- and/or 4-positions.

In another embodiment according to the present invention, the metallocene catalyst component may be described by the formula $$R''(CpR_n)_g M\ X\ Q_{3-g} \quad (II)$$

wherein R'', Cp, Rn, Me and Q have already been defined and wherein X is an hetero atom ligand with one or two lone pair electrons and selected from the group VA or VIA. Preferably, X is nitrogen, phosphorus oxygen or sulfur and it can be substituted or unsubstituted.

The catalyst system of the present invention is not limited provided that it comprises at least one metallocene catalyst component as defined above. The system may comprise further catalyst components if necessary, such as other metallocene catalyst components according to the present invention or other catalysts.

The catalyst system of the present invention comprises, in addition to the above catalyst component, one or more activating agents having an ionising action and capable of activating the matallocene catalyst component. Typically, the activating agent comprises an aluminium- or a boron-containing compound. Suitable aluminium-containing activating agents comprise an alumoxane, an alkyl aluminium compound and/or a Lewis acid.

Preferably, alumoxane is used as an activating agent. The alumoxanes that can be used in the present invention are well known and comprise oligomeric and/or cyclic alkyl alumoxanes represented by the formula

for oligomeric, linear alumoxanes, and

for oligomeric, cyclic alumoxanes, wherein n is 1-40, preferably 10-20, m is 3-20, preferably 3-20 and R is a $C_1$-$C_8$ alkyl group and preferably methyl.

Generally, in the preparation of alumoxanes from, for example, aluminium trimethyl and water, a mixture of linear and cyclic compounds is obtained.

Methylalumoxane is preferably used.

Suitable boron-containing compounds activating agents may comprise triphenylcarbenium boronate, such as tetrakis-pentafluorophenyl-borato-triphenylcarbenium as described in EP-A-0,427,696

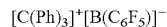

or those of the general formula below as described in EP-A-0,277004 (page 6, line 30 to page 7, line 7):

Additionally, activating agents such as hydroxy isobutyl aluminoxane and metal aluminoxinates can be used in the present invention. These are disclosed for example in Watanabi et al. (Watanabi M, McMahon N. C., Harlan J. C., Barron A. R., in "Reaction of trimethylaluminum with [($^t$Bu)Al (μ$_3$-O)]$_6$: hybrid tert-butylmethylalumoxanes as cocatalysts for olefin polymerisation." In Organometallics, 20, 460-467, 2001.) or in Francis et al. (Francis J. A., Bott S. G. and Barron A. R., in "Are intramolecularly stabilised compounds of aluminium suitable structural models of the $S_N2$ transition state? Molecular structure of [($^t$Bu)$_2$Al (μ-OC$_6$H$_4$-2-OMe)]$_2$." In Polyhedron, 18, 2211-2218, 1999.) or in Francis et al. (Francis J. A., Bott S. G. and Barron A. R., in "Hydroalumination of $H_2C$=$CHCH_2SMe$: Synthesis and molecular structure of ($^t$Bu)$_2$Al(CH$_2$CH$_2$CH$_2$SMe)." In Main Group Chemistry, 3, 53-57, 1999.). With these two new classes of activating agents, it is preferred that at least one Q, in the general formulae (I) and (II) for the metallocene catalyst component, be an alkyl.

When alumoxane is not used as activating agent, one or more aluminiumalkyl represented by the formula AlR$_X$ are used wherein each R is the same or different and is selected from halides or from alkoxy or alkyl groups having from 1 to 12 carbon atoms and x is from 1 to 3. Especially suitable aluminiumalkyl are trialkylaluminium, the most preferred being triisobutylaluminium (TIBAL).

Optionally, a cocatalyst such as an aluminiumalkyl, can be used in addition to alumoxane.

The catalyst system may be employed in a solution polymerisation process, which is homogeneous, or a slurry process, which is heterogeneous. In a solution process, typical solvents include hydrocarbons having from 4 to 7 carbon atoms such as heptane, toluene or cyclohexane. In a slurry process it is necessary to immobilise the catalyst system on an inert support, particularly a porous solid support such as talc, inorganic oxides and resinous support materials such as polyolefins. Preferably, the support material is an inorganic oxide in its finely divided form.

Suitable inorganic oxide materials that may be employed in accordance with this invention include group IIA, IIIA, IVA, or IVB metal oxides such as silica, alumina and mixtures thereof. Other inorganic oxides that may be employed either alone or in combination with the silica, or alumina are for example magnesia, titania or zirconia.

Other suitable support materials comprise for example finely divided functionalised polyolefins such as finely divided polyethylene.

Preferably, the support is a silica support having a specific surface area of from 200 to 700 m$^2$/g and a pore volume of from 0.5 to 3 ml/g.

The amount of activating agent and metallocene component usefully employed in the preparation of the solid supported catalyst system can vary over a wide range. If alumoxane is used as activating agent, the aluminium to transition metal ratio is preferably in the range of from 1:1 to 100:1, more preferably in the range of from 5:1 to 50:1.

The order of addition of the catalyst and alumoxane to the support material can vary. In accordance with a preferred embodiment of the present invention, alumoxane dissolved in a suitable inert hydrocarbon solvent is added to the support material slurried in the same or another suitable hydrocarbon liquid and thereafter the catalyst component is added to the slurry.

Preferred solvents include mineral oils and the various hydrocarbons which are liquid at reaction temperature and which do not react with the individual ingredients. Illustrative examples of the useful solvents include the alkanes such as pentane, iso-pentane, hexane, heptane, octane and nonane; cycloalkanes such as cyclopentane, cyclohexane, and aromatics such as benzene, toluene, ethylbenzene and diethylbenzene.

Preferably, the support material is slurried in toluene and the catalyst component and alumoxane are dissolved in toluene prior to addition to the support material.

The present invention further discloses a process for preparing a catalyst system that comprises the steps of:
A. providing a metallocene catalyst component of the general formula

   (I)

or

   (II)

wherein
each Cp is a substituted or unsubstituted cyclopentadienyl ring with the bridge-head position of at least one of the cyclopentadienyl rings being occupied by a silicon atom;
each R is the same or different and is hydrogen or a hydrocarbyl radical such as alkyl, alkenyl, aryl, alkylaryl or arylalkyl radical containing from 1 to 20 carbon atoms or two carbon atoms are joined together to form a C4-C6 ring;
R" is a structural bridge between two Cp rings;
M is a group IIIB, IVB, VB or VIB metal;
Q is a hydrocarbyl radical such as aryl, alkyl, alkenyl, alkylaryl or arylalkyl radical having from 1 to 20 carbon atoms, a hydrocarboxy radical having from 1 to 20 carbon atoms or a halogen and can be the same or different from each other;
s is 0 or 1, g is 0, 1 or 2 and s is 0 when g is 0, n is 4 when s is 1 and n is 5 when s is 0;
X is an heteroatom ligand with one or two lone pair electrons and selected from group VA or VIA, substituted or unsubstituted.
B. activating the metallocene component with an activating agent having an ionising action;
C. optionally immobilising the catalyst system on an inorganic support.

These metallocene components can be used to produce highly performing systems in the catalytic production of polyethylene, isotactic or syndiotactic polypropylene, polystyrene, homo- and co-polymers of alpha-olefins. They can be used to produce stereo- or non-stereo-regular polymers or macro chains with new polymeric properties. The metallocene catalyst system is selected according to the desired polymer properties. For example, if a syndiotactic polypropylene is desired, the metallocene catalyst component preferably has bilateral Cs symmetry such as for example in the fluorenyl-type group. If an isotactic polypropylene is prepared, the metallocene catalyst component preferably has C2 symmetry such as for example in the indenyl-type group.

The present invention also discloses a process for the preparation of polyolefins including the steps of:
A. selecting a catalyst system comprising:
  1. a metallocene catalyst component of the general formula

   (I)

or

   (II)

wherein
each Cp is a substituted or unsubstituted cyclopentadienyl ring with the bridge-head position of at least one of the cyclopentadienyl rings being occupied by a silicon atom;
each R is the same or different and is hydrogen or a hydrocarbyl radical such as alkyl, alkenyl, aryl, alkylaryl or arylalkyl radical containing from 1 to 20 carbon atoms or two carbon atoms are joined together to form a C4-C6 ring;
R" is a structural bridge between two Cp rings;
M is a group IIIB, IVB, VB or VIB metal;
Q is a hydrocarbyl radical such as aryl, alkyl, alkenyl, alkylaryl or arylalkyl radical having from 1 to 20 carbon atoms, a hydrocarboxy radical having from 1 to 20 carbon atoms or a halogen and can be the same or different from each other;
s is 0 or 1, g is 0, 1 or 2 and s is 0 when g is 0, n is 4 when s is 1 and n is 5 when s is 0,
X is an heteroatom ligand with one or two lone pair electrons and selected from the group VA or VIA, substituted or unsubstituted.
  2. an activating agent having an ionising action;
  3. an optional inorganic support
B. optionally providing a co-catalyst;
C. introducing the catalyst system and optional co-catalyst into a polymerisation zone containing an olefin monomer and an optional co-monomer and maintaining the reaction zone under polymerisation conditions;
D. extracting the desired polymer.

The conditions employed for polymerisation are not particularly limited, provided they are sufficient to effectively polymerise the particular monomer used as a starting material. Optionally pre-polymerisation can be carried out. Preferably, polymerisation takes place in the presence of, hydrogen and an alkene co-monomer such as 1-butene or 1-hexene.

EXAMPLES

The preparation and some uses of dianions of silapentadiene, silafluorene and silaindene are disclosed in Liu et al. (Liu Y., Stringfellow T. C., Ballweg D., Guzei I. A., West R., in "Structure and chemistry of 1-silafluorenyl dianion, its derivatives, and an organosilicon diradical dianion." J. Am. Chem. Soc., 124, 49, 2002.).

In the present invention, these dianions were used to prepare metallocene-catalyst components by any method known in the art such as disclosed for example in EP-A-0, 426,643 or in EP-A-0,619,325, or in EP-A-0,910591.

Examples of such metallocene catalyst components are disclosed in FIGS. 1 to 3.

Figure 1:
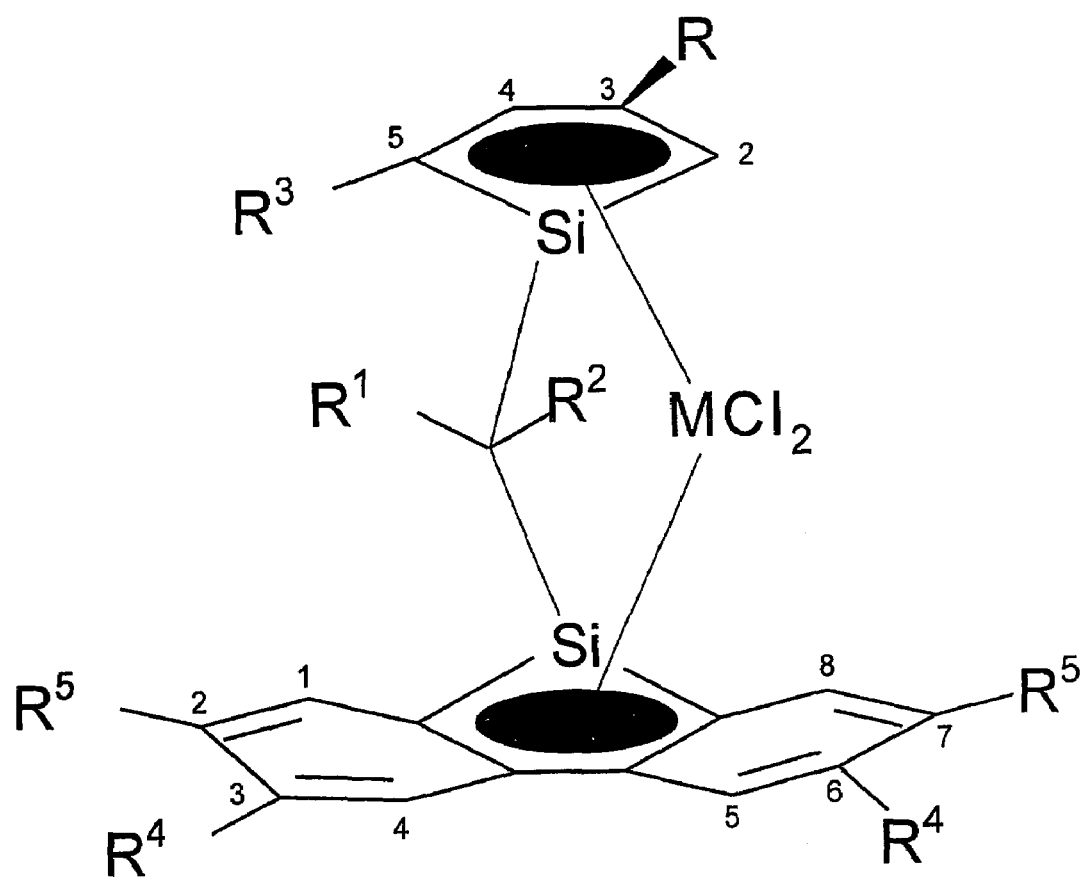
FIG. 1 represents a bridged cyclopentadienyl-fluorenyl structure wherein the carbon atom has been replaced by a silicon atom at the bridgehead position of both cyclopentadienyls.
Figure 2:
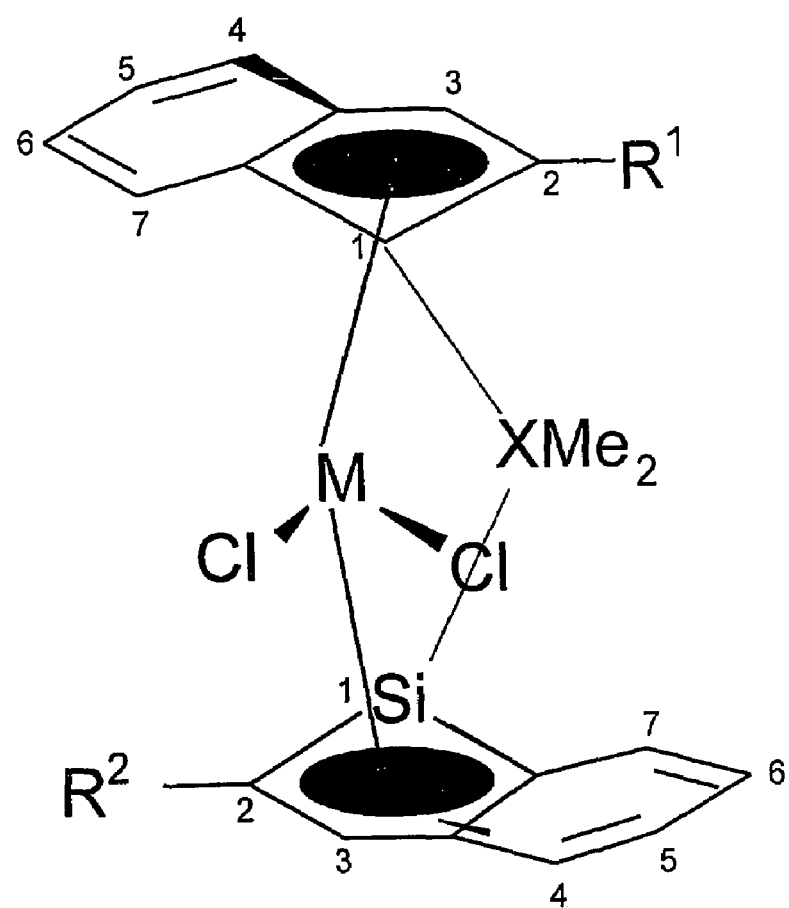
FIG. 2 represents a bridged bisindenyl structure wherein the carbon atom has been replaced by a silicon atom at the bridgehead position of one of the cyclopentadienyls.
Figure 3:
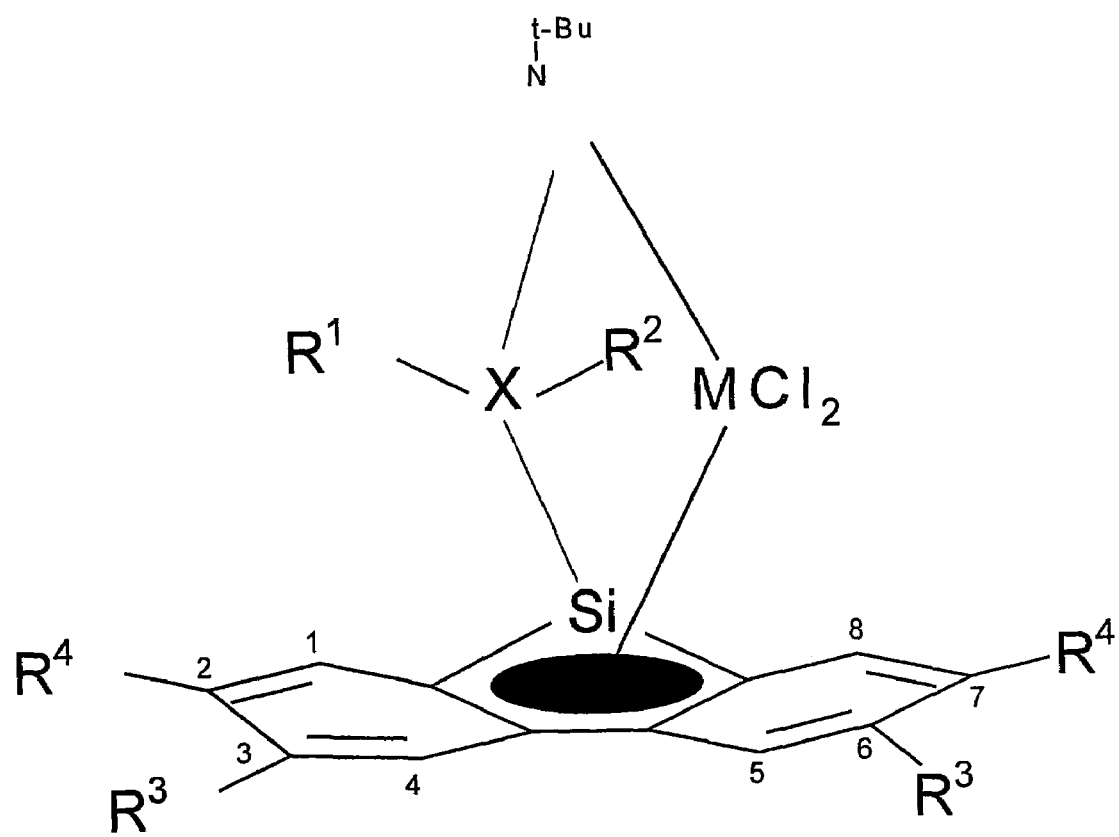
FIG. 3 represents a constrain geometry structure wherein the carbon atom has been replaced by a silicon atom at the bridgehead position of the fluorenyl.

To produce an active catalyst system, the metallocene catalyst component was reacted with methylalumoxane (30 wt % in toluene), under the usual conditions to give a solution of the corresponding cation and the anionic methylalumoxane oligomer.

Then the resulting solution comprising the metallocene cation and the anionic methylalumoxane oligomer was added to a support.

The invention claimed is:

1. A metallocene catalyst component for producing polyolefins according to formula (I):

$$R''(CpR_n)_g(CpR_n)M\ Q_{3-g} \quad (I)$$

or according to formula (II):

$$R''(CpR_n)_g M\ X\ Q_{3-g} \quad (II)$$

wherein:
each Cp is a substituted or unsubstituted cyclopentadienyl ring with a bridge-head position of at least one of the cyclopentadienyl rings being occupied by a silicon atom;
each R is the same or different and is hydrogen or a hydrocarbyl radical containing from 1 to 20 carbon atoms or two carbon atoms are joined together to form a $C_4$-$C_6$ ring;
R" is a structural bridge between two Cp rings or between a Cp ring and a heteroatom ligand X;
M is a group IIIB, IVB, VB or VIB metal from the Periodic Table of Elements;
Q is a hydrocarbyl radical having from 1 to 20 carbon atoms, a hydrocarboxy radical having from 1 to 20 carbon atoms or a halogen and can be the same or different from each other;
n is an integer from 0 to 4;
g is 1 or 2; and
X is a heteroatom ligand with one or two lone pair electrons and selected from the elements in group VA or VIA from the Periodic Table of Elements.

2. The metallocene catalyst component of claim 1 wherein the number of substituents on each cyclopentadienyl ring is no more than two.

3. The metallocene catalyst component of claim 1 comprising:
(a) at least one cyclopentadienyl group having at least one substituent at the 3 or 5 position; or
(b) at least one fluorenyl group having at least one substituent at the 3 or 6 position or at the 2 or 7 position; or
(c) at least one indenyl group having at least one substituent at the 2 or 4 position.

4. The metallocene catalyst component of claim 3 comprising:
(a) at least one cyclopentadienyl group having two substituents at the 3 and 5 positions; or
(b) at least one fluorenyl group having two substituents at the 3 and 6 positions or at the 2 and 7 positions; or
(c) at least one indenyl group having two substituents at the 2 and 4 positions.

5. The metallocene catalyst component of claim 3 wherein R" is an ethylene or dimethylsilyl group.

6. The metallocene catalyst component of claim 5 wherein M is zirconium or titanium.

7. The metallocene catalyst component of claim 6 wherein Q is chlorine.

8. The metallocene catalyst component of claim 1 wherein the heteroatom ligand X is selected from the group consisting of nitrogen, phosphorus, oxygen and sulfur.

9. The metallocene catalyst component of claim 1 conforming to formula (I) in which one Cp is a cyclopentadienyl group and another Cp is a fluorenyl group to provide a bridged cyclopentadienyl-fluorenyl ligand structure in which the bridgehead position of at least one of said fluorenyl and said cyclopentadienyl is occupied by a silicon atom.

10. The metallocene catalyst component of claim 9 wherein the bridgehead position of said fluorenyl-type group is occupied by a silicon atom.

11. The metallocene catalyst component of claim 10 wherein the bridgehead position of said cyclopentadienyl group is occupied by a silicon atom.

12. The metallocene catalyst component of claim 11 wherein said fluorenyl group has at least two substituents at the 2 and 7 positions or at the 3 and 6 positions.

13. The metallocene catalyst component of claim 12 wherein said cyclopentadienyl group is substituted at at least one of the 3 and 5 positions.

14. The metallocene catalyst component of claim 13 wherein said cyclopentadienyl group has two substituents at the 3 and 5 positions.

15. The inetallocene catalyst component of claim 1 conforming to formula (I) in which each of said Cp's is an indenyl group to provide a bridged bis-indenyl ligand structure in which the bridgehead position of at least one of said indenyl groups is occupied by a silicon atom.

16. The metallocene catalyst component of claim 15 wherein each of said indenyl groups is substituted at the 2 position.

17. The metallocene catalyst component of claim 1 conforming to formula (II) in which $CpR_n$ is a fluorenyl group in which the bridgehead position of said fluorenyl group is occupied by a silicon atom.

18. The metallocene catalyst component of claim 17 wherein said fluorenyl group has at least two substituents at the 2 and 7 positions or at the 3 and 6 positions.

19. A metallocene catalyst system comprising the metallocene catalyst component of claim 1 and further comprising an activating agent having an ionizing action.

20. The metallocene catalyst system of claim 19 wherein the activating agent is alumoxane.

21. The metallocene catalyst system of claim 19 wherein the alumoxane is methylalumoxane.

22. The metallocene catalyst system of claim 19 further comprising an inert inorganic support.

23. The metallocene catalyst system of claim 22 wherein the inorganic support is silica having a specific surface area within the range of 200-700 $m^2$/g and a pore volume within the range of 0.5-3 ml/g.

24. A process for the polymerization of an olefin comprising:
   (a) providing a metallocene catalyst system comprising:
      (1) a metallocene catalyst component for producing polyolefins according to formula (I):

$$R''(CpR_n)_g(CpR_n)M\ Q_{3-g} \qquad (I)$$

or according to formula (II):

$$R''(CpR_n)_gM\ X\ Q_{3-g} \qquad (II)$$

wherein:
         each Cp is a substituted or unsubstituted cyclopentadienyl ring with a bridge-head position of at least one of the cyclopentadienyl rings being occupied by a silicon atom;
         each R is the same or different and is hydrogen or a hydrocarbyl radical containing from 1 to 20 carbon atoms or two carbon atoms are joined together to form a $C_4$-$C_6$ ring;
         R'' is a structural bridge between two Cp rings or between a Cp ring and a heteroatom ligand X;
         M is a group IIIB, IVB, VB or VIB metal from the Periodic Table of Elements;
         Q is a hydrocarbyl radical having from 1 to 20 carbon atoms, a hydrocarboxy radical having from 1 to 20 carbon atoms or a halogen and can be the same or different from each other;
         n is an integer from 0 to 4;
         g is 1 or 2; and
         X is a heteroatom ligand with one or two lone pair electrons and selected from the elements in group VA or VIA from the Periodic Table of Elements; and
      (2) an activating agent for said metallocene catalyst component having an ionization action;
   (b) introducing an alpha olefin and said metallocene catalyst system into a polymerization reaction zone;
   (c) maintaining said reaction zone under polymerization conditions and polymerizing said alpha olefin to produce a polymer of said alpha olefin; and
   (d) extracting said polymer from said reaction zone.

25. The process of claim 24 wherein said alpha olefin comprises ethylene and the polymer recovered from said reaction zone is polyethylene.

26. The process of claim 24 wherein said alpha olefin comprises propylene and the polymer recovered from the reaction zone is selected from the group consisting of isotactic polypropylene and syndiotactic polypropylene.

* * * * *